(12) United States Patent
Yao et al.

(10) Patent No.: US 7,002,687 B2
(45) Date of Patent: Feb. 21, 2006

(54) QUANTITATIVE SCANNING ANALYZER UNIT

(75) Inventors: Wen-Fa Yao, Hsinchu (TW);
Chih-Ming Wang, Hsinchu (TW);
Yung-Chuan Liu, Hsinchu (TW);
Shih-Yang Lo, Hsinchu (TW); Roger Lai, Hsinchu (TW); Kuang-Pin Hsiung, Hsinchu (TW)

(73) Assignee: Taiwan Unison Biotechnology Co., Ltd., Hsinchu (TW)

( * ) Notice: Subject to any disclaimer, the term of this patent is extended or adjusted under 35 U.S.C. 154(b) by 436 days.

(21) Appl. No.: 10/033,883

(22) Filed: Dec. 27, 2001

(65) Prior Publication Data

US 2003/0123062 A1    Jul. 3, 2003

(51) Int. Cl.
*G01J 3/46* (2006.01)

(52) U.S. Cl. .................... 356/402; 356/420; 356/425

(58) Field of Classification Search ............... 356/408, 356/409, 414, 418, 420, 425, 402
See application file for complete search history.

(56) References Cited

U.S. PATENT DOCUMENTS

| 4,554,460 A | * | 11/1985 | Klein ...................... 250/208.2 |
| 4,935,875 A | * | 6/1990 | Shah et al. .................... 702/22 |
| 5,216,597 A | * | 6/1993 | Beckers ........................ 356/39 |
| 5,231,576 A | * | 7/1993 | Suzuki et al. ................. 356/39 |

* cited by examiner

*Primary Examiner*—Gregory J. Toatley, Jr.
*Assistant Examiner*—Roy M. Punnoose
(74) *Attorney, Agent, or Firm*—J.C. Patents

(57) ABSTRACT

A scanning analyzer unit comprises a scanner device, a signal amplifier, an analog/digital converter, a driver device, a controller device, a computing unit, and a RS-232 interface. After chemical, biological, or chemi-enzymatic reaction, a resulting color change of a testing support through reacted multi-chromogens therein is quantified by means of the scanning analyzer unit. Via the sensitivity differences of the multi-chromogens at a fixed wavelength of the scan, multi-analyte concentrations of wide range variations in one sample can be simultaneously assayed.

4 Claims, 3 Drawing Sheets

QUANTITATIVE SCANNING ANALYZER UNIT

BACKGROUND OF THE INVENTION

1. Field of the Invention

The invention relates to chemical, medical, and biotechnological testing methods. More particularly, the invention relates to a scanning analyzer unit suitable that provides quantitative testing results in agricultural food processing, environmental pollution monitoring, clinical point-of-care testing, and other biotechnological applications.

2. Description of the Related Art

Regardless the location or the manner accomplished, chemical and biochemical analysis methods are fully described in terms of their performance characteristics. The performance characteristics principally are accuracy, sensitivity, specificity, rapidity, easiness, and economy. Accuracy, sensitivity, and specificity usually characterize the reliability of the analyses while rapidity, easiness, and economy characterize the practicability of the analyses.

In agriculture, food processing, environmental pollution management, and in-vitro clinical diagnosis, analysis performance generally emphasizes on reliability characteristics while practicability aspects are less considered. However, in many specific situations where chemical and biochemical analyses must be performed on site, the practicability of the analysis methods becomes an important factor.

With the example of pesticide residual, in-field, pre-market, and on-line process analyses conventionally require on-site equipment to monitor the concentration of pesticide residues in vegetables, fruits, dairy, meat, and relevant products. Currently, on-site analytical equipment mostly provides qualitative results; the resulting observation is therefore less meaningful than the observation provided by laboratory equipment and methodologies. Moreover, because pesticide contamination of agricultural products and ground water usually needs multi-targets detection, on-site multi-quantitative testing equipment is therefore required.

In clinical in-vitro diagnosis (IVD), additional to reliability requirement, the rapidity of obtention of the test results is even more crucial than in the case of environmental and agricultural management. The consideration of rapidity and other efficiency factors in clinical testing is known as point-of-care testing (POCT). POCT has typically evolved from a demand for short turn-around-time (STAT) analytical results to be available from sources other than typical central laboratories. By bringing analysis systems closer to the patients, the obtention of STAT results is facilitated, which improves the medical treatments and benefits the patients.

With respect to POCT, rapidity and easiness are considered as prevalent practicability factors while sensitivity and specificity are prevalent reliability factors. POCT systems are usually demanded in hospital locations such as emergency rooms, intensive care units, operation rooms, cardial pulmonary rooms, recover rooms, or even in ambulances. POCT systems are also demanded in many relevant clinical locations.

A representative example of POCT systems is that which uses multi-marker components. Results provided by POCT multi-marker enable precise, accurate, and early diagnosis of certain diseases. The POCT supports that use multi markers may appear under various forms such as paper testing or test kits where samples are put in contact with the markers. The testing results usually consist of color or aspect change signals that are evaluated through the physician's perception. Taking the example of prostate specific antigen (PSA) tests, both complex and free PSA are quantitatively measured to distinguish prostate hyperplasia and malignancy. For acute myocardial infarction (AMI), three specific cardiac markers, that are myoglobin, creatine kinase MB, and troponins (I or T, or fatty acid binding protein), are usually quantified for disease triage, therapeutic intervention and monitoring of therapeutic outcome. However, in the case of PSA, the concentrations of complex and free PSA between normal persons and patients with prostate cancer vary from the level of micrograms to the level of sub-nanograms. In the case of AMI, the concentration differences of these clinical markers between the normal persons and sick patients vary even more than in the case of PSA: they may vary from the level of milligrams to the level of sub-nanograms. It is therefore difficult to differentiate the concentrations of these disease markers by only observing the reflectance changes of one single chromogenic compound in POCT quantitative immunoassay.

SUMMARY OF THE INVENTION

A first aspect of the invention is therefore to provide a multiple scanning analyzer unit that provides immediate and objective quantitative results from conventional testing supports that deliver scannable results. As a result, adequate actions can be taken to manage environmental pollution, agricultural product contamination, and therapeutical intervention.

Furthermore, another aspect of the invention is to provide a portable scanning analyzer unit that can analyze the results of the testing supports so that the responses can be more conveniently justified on sites.

Yet, another aspect of the invention is to provide a scanning analyzer unit that can scan testing supports to provide quantitative results so that the testing supports are more accurately used.

To accomplish the foregoing and other objectives, a portable scanning analyzer unit of the invention, suitable for use with a testing support delivering qualitative test results, comprises a scanner device, a signal amplifier, an analog/digital converter, a control device, a driver device, a computing unit, and a RS-232 interface. After a sample to be tested has reacted with the testing support, the testing support is scanned within the scanning analyzer unit via the scanner device. The scan of the testing support is driven via the driver device. The scanner device produces a resulting test signal that is amplified via the signal amplifier, and converted into a digital signal via the analog/digital converter. The digital signal is delivered to the computing unit for analysis. In addition, the computing unit is coupled with the control device to control the drive of the scanning operation. The RS-232 interface enables data transfer between the scanning analyzer unit and other data storage means and/or computers for further processing operations.

With the above portable scanning analyzer unit, multiple and quantitative results are advantageously obtained from qualitative testing supports.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
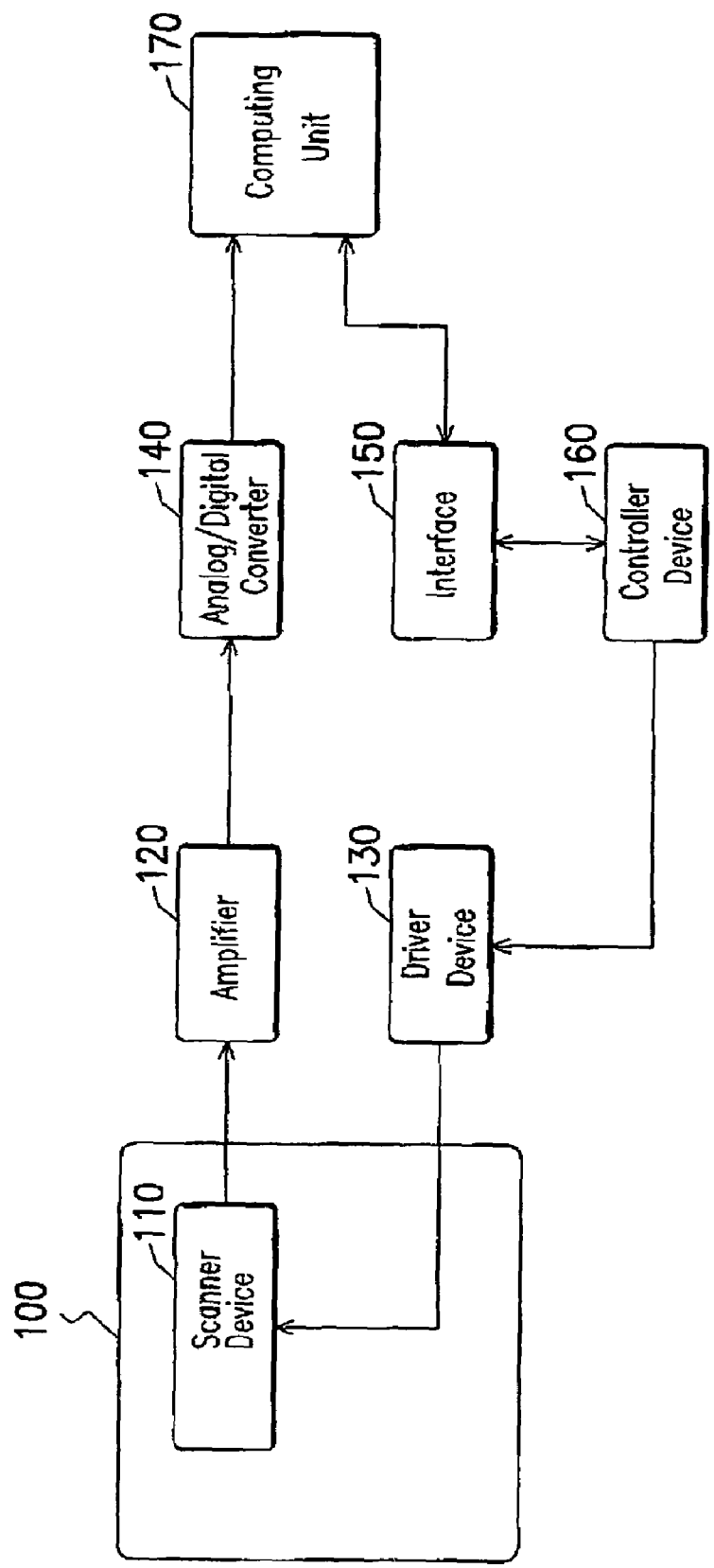
FIG. 1 is a block diagram schematically showing a scanning analyzer unit according to an embodiment of the invention.

Referring now to FIG. 1, a block diagram schematically illustrates various component devices of a scanning analyzer unit according to an embodiment of the invention. The scanning analyzer unit of the invention can advantageously accommodate various types of testing supports. The testing supports may include, for example, conventional testing kits that display qualitative testing results on a display window. "Qualitative testing results" refer to the change signal that is typically generated by the testing reaction, and can be observed.

After a sample has reacted with the testing support, the testing support is placed within the scanning analyzer unit 100 to be scanned via a scanner device 110. The results on the testing support typically appear as color separation if analytes are present in the sample. Although any fast forming coloring agents may be theoretically used as chromogens in the testing support to indicate the presence of analytes, broad spectra of colored latex beads, dyed antigens and antibodies are more conventionally used. Furthermore, the chromogens in the chemical or biochemical reaction can be manipulated to match the analyte concentrations in the purpose of one step determination of multi-analytes in the sample. The scanner device 110 generates a single or a plurality of incident monochromatic lights from a, for example, yellow-green LED or/and red-green-blue (RGB) LED array, that reach the surface of the testing support where reacted chromogens are present. Although the above wavelengths of monochromatic lights are preferably used in the present embodiment, other wavelengths of monochromatic lights may be also used in accordance with the needs of specific applications. In accordance with their chemical structures, the chromogens partially absorb the monochromatic lights while other parts of the monochromatic lights are reflected and measured via a contact image sensor (not shown) in the scanner device 110. The reflected parts are inversely proportional to the chromogens concentrations. The highest sensitivity is obtained when measuring at the maximal absorbance of the to-be-scanned chromogens. The scanner device 110 produces a resulting test signal corresponding to the test results scanned on the testing support. Various mechanical devices (not shown) are mounted within the scanning analyzer unit to adequately drive the scan of the testing support. In the present embodiment, a driver device 130 that may be, for example, a stepping motor, drives the scan of the testing support held by a holding member (not shown).

The test signal produced by the scanner device 110 is amplified via a signal amplifier 120, and transferred to an analog/digital converter 140. The analog/digital converter 140 converts the test signal into a digital signal that is delivered to a computing unit 170 to be analyzed and obtain further results of the test. According to specific needs, the computing unit 170 can be, for example, a portable computer, a personal computer, or a single chip data processing unit.

The computing unit 170 is further coupled with a controller device 160 via an interface 150, while the controller device 160 is coupled with the driver device 130. The computing unit 170 thereby controls the drive of the driver device 130 via the controller device 160 and interface 150. The interface 150 may be, for example, a standard RS-232 interface that enables effective signal transfer between the computing unit 170 and the controller device 160. The controller device 160 may be, for example, a microprocessor that delivers a driver signal to the driver device 130.

The above scanning analyzer unit is preferably constructed into a portable form so that data of multi-analytes can be rapidly and accurately obtained on site, and appropriate actions therefore can be immediately taken. As a result, the present invention is particularly advantageous when, for example, STAT results are necessary to rapidly take adapted treatments and prevent disease progression, or immediate testing of a sample is necessary to avoid damageable conservation of the sample. Hence, the scanning analyzer unit can be implemented into IVD equipment for efficient medical intervention as well as powerful tool in environmental and food processing management of multi-analytes with wide concentration ranges present in one sample.

Figure 2A:
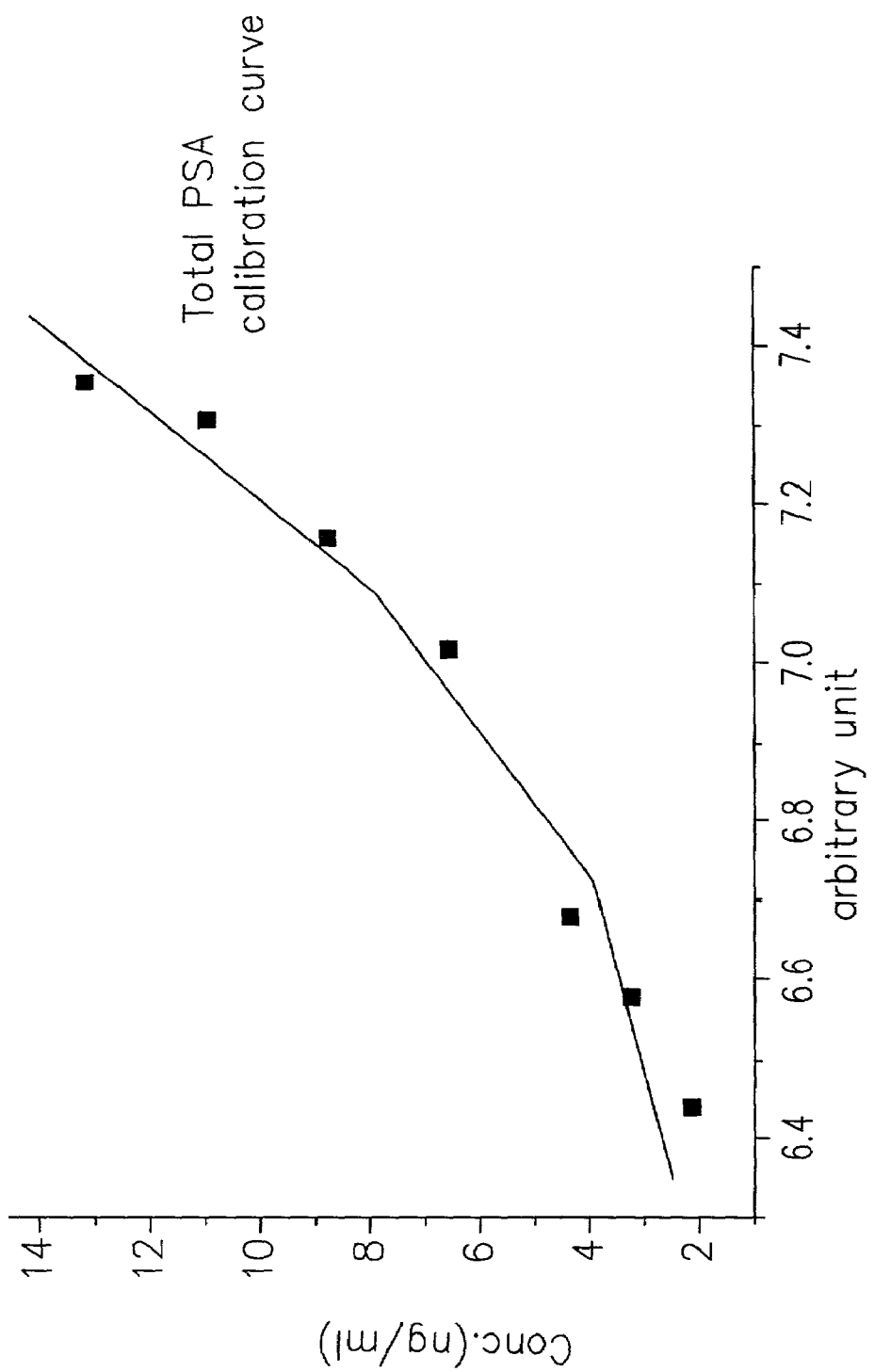
FIG. 2A and FIG. 2B are schematic graphs plotting the calibration curves obtained with a scanning analyzer unit of the invention.
Figure 2B:
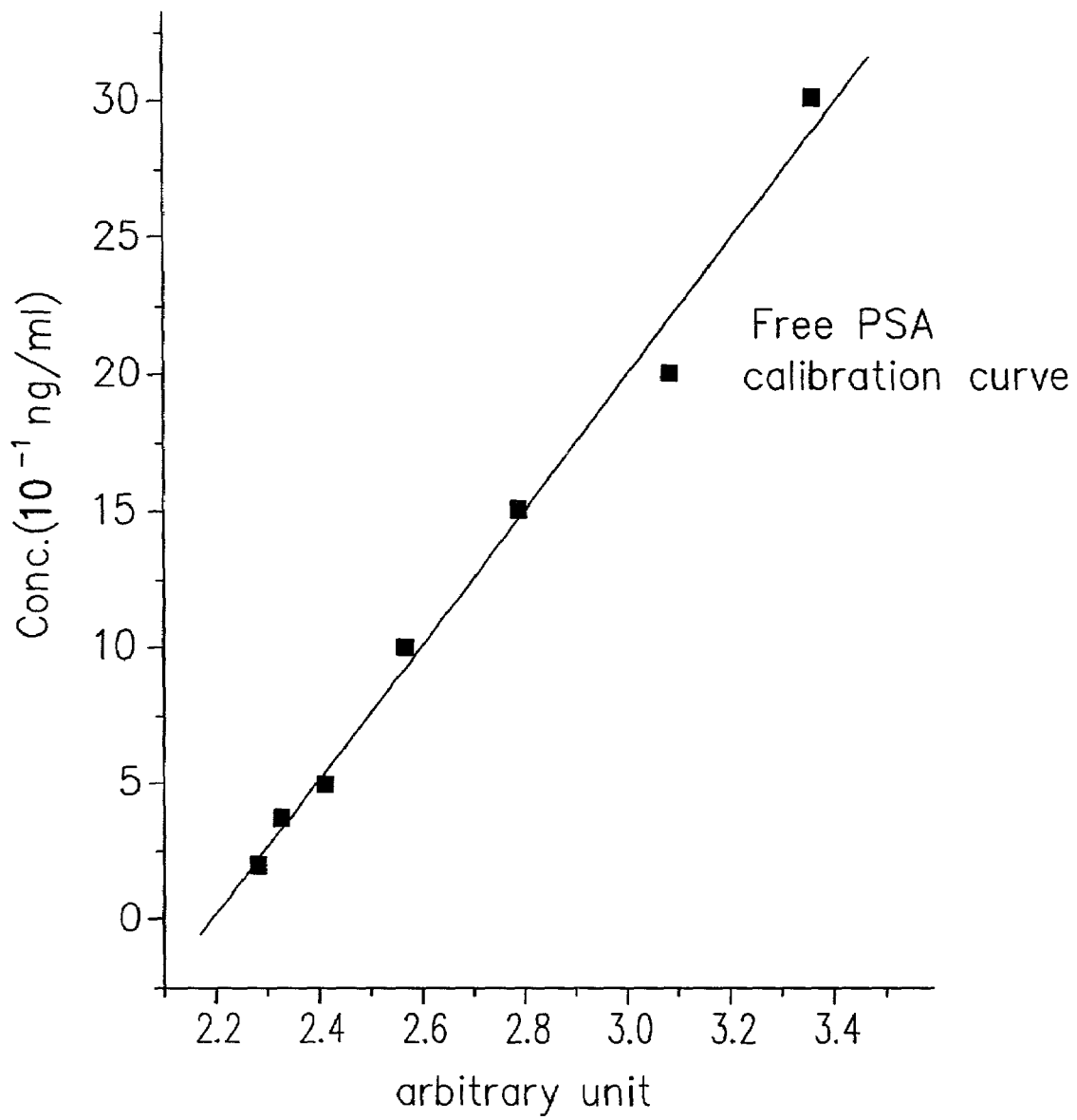

Referring to FIG. 2A and FIG. 2B, two graphs schematically plot the calibration curves of PSA concentrations obtained with the scanning analyzer unit of the invention. The PSAs have been tested via a testing support that was placed in the scanning analyzer unit of the invention after color separation. Provided with the above specific calibration curve, a physician can thereby provide a more accurate and immediate diagnosis of prostate hyperplasia and malignancy. Practically, in current applications, the scanning analyzer unit of the invention can accomplish a measurement over six orders of magnitude ranges of multi-analytes concentrations in one sample.

In conclusion, the foregoing description of embodiments and examples of the invention presents at least the following features and advantages. The scanning analyzer unit of the invention, constructed in a portable form, can perform testing and obtain immediate quantitative results on site, which favorably reduces the time interval that separates the moment when testing is taken and the moment when the managerial action is effectively taken. Furthermore, the portable scanning analyzer unit of the invention can be adapted with specific types of testing supports to provide various dedicated testing systems. Those dedicated testing systems may be used in, for example, AMI testing, prostate cancer scanning, drug abuses, pediatric diseases, therapeutic drug monitoring, venereal disease testing, etc, where multi-analytes quantification is needed to accomplish disease diagnoses and monitoring.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A scanning analyzer unit, for analyzing a sample in a testing support, the scanning analyzer unit comprising:
   a scanner device, for scanning the testing support suitable for supporting a reaction of analytes in the sample to achieve a color separation, wherein the scanner device outputs a test signal corresponding to concentrations of the analytes in response to scanning of the testing support after the reaction of the analytes, and wherein the scanner device comprises a light emission diode (LED) array;

a signal amplifier coupled to the scanner device to amplify the test signal;

an analog/digital converter coupled to the signal amplifier, wherein the analog/digital converter converts the amplified test signal into a digital test signal;

a computing unit, coupled to the analog/digital converter, for receiving and analyzing the digital test signal to output a control signal and to obtain concentration values of the analytes;

a controller device, coupled to the computing unit, for receiving the control signal and outputting a driver signal according to the control signal; and a stepping motor, coupled to the controller device and the scanner device, for receiving the driver signal and driving the scanner device to measure the concentrations of the analytes.

2. The scanning analyzer unit of claim 1, further comprising an interface placed between the computing unit and the controller device to enable signal transfer between the computing unit and the controller device.

3. The scanning analyzer unit of claim 2, wherein the interface is a standard RS-232 interface.

4. The scanning analyzer unit of claim 1, wherein the sample is of chemical or biological nature.

* * * * *